United States Patent [19]

Miller et al.

[11] Patent Number: 5,567,385
[45] Date of Patent: Oct. 22, 1996

[54] STERILANT COMPOSITION

[75] Inventors: Charles R. Miller, Houston; Haskell B. Berry, Jr., Channelview, both of Tex.

[73] Assignee: Premier Medical Technology, Inc., Houston, Tex.

[21] Appl. No.: 505,920

[22] Filed: Jul. 24, 1995

(Under 37 CFR 1.47)

Related U.S. Application Data

[63] Continuation of Ser. No. 174,297, Dec. 23, 1993, abandoned.

[51] Int. Cl.⁶ .............................. A01N 25/14; A61L 2/16; C02F 1/68; C11D 7/20
[52] U.S. Cl. .............................. 422/28; 210/751; 210/764; 510/161; 510/319
[58] Field of Search ........................... 422/28; 210/764, 210/751; 588/252, 258; 252/156, 106

[56]  References Cited

U.S. PATENT DOCUMENTS

| | | | |
|---|---|---|---|
| 242,777 | 6/1881 | Huet | 564/102 |
| 1,167,360 | 1/1916 | Miner | 424/76.9 |
| 1,728,082 | 7/1929 | Scales | 252/156 |
| 1,745,844 | 2/1930 | Cowles | 252/109 |
| 2,087,592 | 7/1937 | Chestnut | 252/156 |
| 2,251,080 | 7/1941 | Taber | 206/0.5 |
| 3,113,924 | 12/1963 | Mendius, Jr. | 216/608 |
| 3,791,977 | 2/1974 | Ancel et al. | 252/156 |
| 3,850,852 | 11/1974 | Neillie | 252/536 |
| 4,001,030 | 1/1977 | Watson et al. | 106/100 |
| 4,781,842 | 11/1988 | Nicholson | 210/751 |
| 4,783,194 | 11/1988 | Dugenet et al. | 252/103 X |
| 5,013,458 | 5/1991 | Christy, Sr. et al. | 210/751 |
| 5,089,228 | 2/1992 | Meijer | 422/32 X |
| 5,248,486 | 9/1993 | Matsuoka et al. | 422/294 |
| 5,275,733 | 1/1994 | Burnham | 210/609 |

OTHER PUBLICATIONS

National Lime Association, "Poultry House Liming".
National Lime Association, "Lime in Municipal Sludge Processing," Bulletin No. 217. 1980.

*Primary Examiner*—Robert J. Warden
*Assistant Examiner*—E. Leigh Dawson
*Attorney, Agent, or Firm*—Keck, Mahin & Cate

[57] ABSTRACT

A sterilant for rendering non-infectious shredded medical waste operates by alkaline oxidation to break down the pathogens in the medical waste during shredding, rendering the shredded waste product sterile, granular and substantially dry. The sterilant includes an alkaline oxide, such as calcium oxide, and a buffer, such as calcium carbonate including drying agents in the buffer. The sterilant creates a highly alkaline environment, at ambient temperatures, killing all or substantially all pathogens. The effectiveness of the sterilant is not dependent on temperature.

13 Claims, 7 Drawing Sheets

STERILANT COMPOSITION

This is a continuation application of Ser. No. 08/174,297, filed on Dec. 23, 1993, now abandoned.

FIELD OF THE INVENTION

The invention relates to a sterilant composition, particularly a sterilant composition for use in medical waste shredding apparatus which provides an alkaline environment for producing a non-infectious shredded product, and a method of using the sterilant.

BACKGROUND OF THE INVENTION

The use of lime for disinfection is very old and well-known. Lime reacts exothermically. The high temperatures produced kill microorganisms.

U.S. Pat. No. 5,248,486, to Matsuoka et al., describes heat generating agents which are quicklime, calcined dolomite and magnesium oxide, optionally combined with a reaction moderating agent, used for medical waste sterilization. The heat generating agents are in a dry phase which, when mixed with an aqueous phase, generates heat whereby sterilization of medical waste, particularly hypodermic needles, is achieved. The process is maintained at a pH of 6.0–8.5 and a temperature of 40° C.–600° C. for 1 to 90 minutes to effect sterilization by killing microorganisms with the heat produced.

U.S. Pat. No. 3,791,977, to Ancel, describes heavy duty exothermic all-purpose cleaning compositions which also use heat generation to obtain the desired results. The compositions used are based on sodium hydroxide.

U.S. Pat. No. 3,850,852, describes a detergent composition including an alkali metal carbonate, such as sodium carbonate.

Dugenet et al., U.S. Pat. No. 4,783,194, describes a process for bacterial decontamination of textiles using carbonate compounds such as sodium carbonate and sodium sesquicarbonate.

SUMMARY OF THE INVENTION

A sterilant for rendering non-infectious shredded medical waste operates by alkaline oxidation to break down the pathogens in the medical waste during shredding, rendering the shredded waste product sterile, granular and substantially dry. The sterilant includes an alkaline oxide, such as calcium oxide, and a buffer, such as calcium carbonate including drying agents in the buffer. The sterilant creates a highly alkaline environment, at ambient temperatures, killing all or substantially all pathogens. The effectiveness of the sterilant is not dependent on temperature.

A sterilant of the invention is an alkaline composition which reduces and destroys microorganisms in medical waste of all kinds, including body tissues, surgical instruments, surgical clothing, hospital textiles and in other applications by alkaline oxidation of the microorganism structure. The sterilant is a combination of calcium oxide and calcium carbonate, optionally including other compounds, which effects disinfection or sterilization of medical waste, rendering non-infectious all or substantially all pathogens present in the waste at ambient temperatures in a highly alkaline environment. The pH is typically about 10–12.5, preferably 11–12. The sterilant will destroy microbial organisms such as bacteria, viruses, fungi, spore formers and other microorganisms, by contacting in a moist environment at ambient temperature and pH of 10–12.5.

In a typical composition, the sterilant contains calcium oxide and calcium carbonate in approximately a 1:1 ratio. Calcium oxide (CaO) in the sterilant combines with water to form calcium hydroxide ($Ca(OH)_2$). Upon initial contact with microorganisms, the alkaline solution dissolves the outer shell of the target organism, exposing the genetic material (DNA) of the microorganism to the chemical. In this alkaline oxidation process, it is believed that a combination of alkaline reaction and free radical oxygen attacks the DNA and tears apart and dissolves the nuclei of the organism. Any portion not dissolved may be occluded in the surface of the particles remaining, making regrowth impossible. The sterilant kills the pathogens by denaturing nucleic acids and proteins therein.

Reaction time is directly correlated to concentration of $Ca(OH)_2$ volume. The $CaCO_3$ plays a role in providing available surface area for adsorption of any microorganisms onto surface particles. The alkaline environment of the $CaCO_3$ particles may also play a role in destroying the outer shell of the organisms, making the DNA susceptible to attack by the alkaline solution and free radical oxygen.

Colloidal particles present in the sterilant may also play a major role in the ability of the sterilant to kill microorganisms. With a portion of the sterilant particles being of less than one micron in diameter during shredding, the mobility of the chemicals is greatly enhanced and makes coverage of all available surfaces that may contain microorganisms much more accessible to the chemical. Upon contact, the microscopic particles attack the outer shell of the microorganism and break down the inherent defenses thereof. Once the outer shell is penetrated, the DNA has no defense against the alkaline penetration of the solution. As the concentration of hydroxyl ions increases, the resistance by microorganisms decreases. The defenses of the microorganisms are based on the ability to fight off invasion via the outer shell of the microorganism. This outer shell is destroyed by the sterilant. The increase in hydroxyl ions breaks the outer shell through physical colloidal attack and chemical changes caused by increase of hydroxyl ions. The microorganisms have no defense that will withstand this two fold attack.

The sterilant is hygroscopic and has the ability to trap and retain airborne microorganisms that might otherwise elude the physical and chemical reactions. A very high internal surface area provides the product with the ability to adsorb and absorb microorganisms and, because of the alkalinity, the sterilant immediately breaks down and dissolves the DNA in the microorganisms.

DETAILED DESCRIPTION OF THE PREFERRED EMBODIMENTS

The invention herein provides a sterilizing reaction which takes place at ambient temperatures at a high pH, sterilizing medical waste by rendering pathogens non-infectious and preventing regrowth thereof. The reaction operates by alkaline oxidation to break down the pathogen structure in the medical waste during shredding, rendering the shredded waste product non-infectious. The product is shredded in appearance and is preferably substantially dry. The process optimally operates with a minimum of free water content, although higher quantities of liquid may be present. The sterilant includes an alkaline oxide, such as calcium oxide, and a buffer, such as calcium carbonate and may include further drying agents. In a typical batch of incoming medical waste, 5% sterilant may be used with 15–20% water, by weight. The sterilant creates a highly alkaline environment, is hygroscopic and absorbs free water in the shredded product.

A sterilant for rendering non-infectious all or substantially all pathogens in medical waste includes calcium oxide (CaO) and calcium carbonate ($CaCO_3$) mixed in a ratio of about 20:80 to 60:40, preferably about 40:60 to 60:40, by weight which, when mixed with pathogen-containing material and water, reacts to kill pathogens at a pH of about 10–12.5, preferably about 11–12, and a temperature of 5°–35° C., preferably about 20°–35° C. to produce a non-infectious product. If less than 40% CaO is present, a greater quantity of sterilant is needed in the mix. If more than 60% CaO is present, the reaction generally becomes hot and too much steam is produced. The sterilant is generally used at a concentration of 4 to 10% by weight, preferably 5 to 8% by weight. In a medical waste shredder, such as is described in our copending application Ser. No. 08/014,877, filed Feb. 5, 1993, now U.S. Pat. No. 5,346,142, the reaction time (throughput) of the shredder is about 1 to 5 minutes.

The sterilant operates optimally at ambient temperatures, namely at about 5°–35° C. Any cold water supply may be used. The effectiveness of the sterilant does not depend on the temperature.

The sterilant may further include at least one of the following compounds: magnesium oxide, aluminum oxide, silicon dioxide, ferric oxide, calcium sulfate, potassium oxide and titanium dioxide.

A method of rendering pathogen containing waste material non-infectious using the sterilant of the invention includes mixing pathogen-containing shredded waste material with sufficient sterilant to render non-infectious all or substantially all pathogens in the waste material, the sterilant including calcium oxide and calcium carbonate mixed in a ratio of 20:80 to 60:40, by weight, reacting the sterilant with the pathogen-containing material and water at a pH of about 10–12.5 and a temperature of 5°–35° C., killing all or substantially all the pathogens and producing a non-infectious substantially dry, shredded product. In this method, pathogens are killed by denaturing the nucleic acids and proteins in the pathogens with the alkaline sterilant. The sterilant mixture may optionally also include at least one further reactant selected from magnesium oxide, aluminum oxide, silicon dioxide, ferric oxide, calcium sulfate, potassium oxide and titanium dioxide.

Figure 1A:
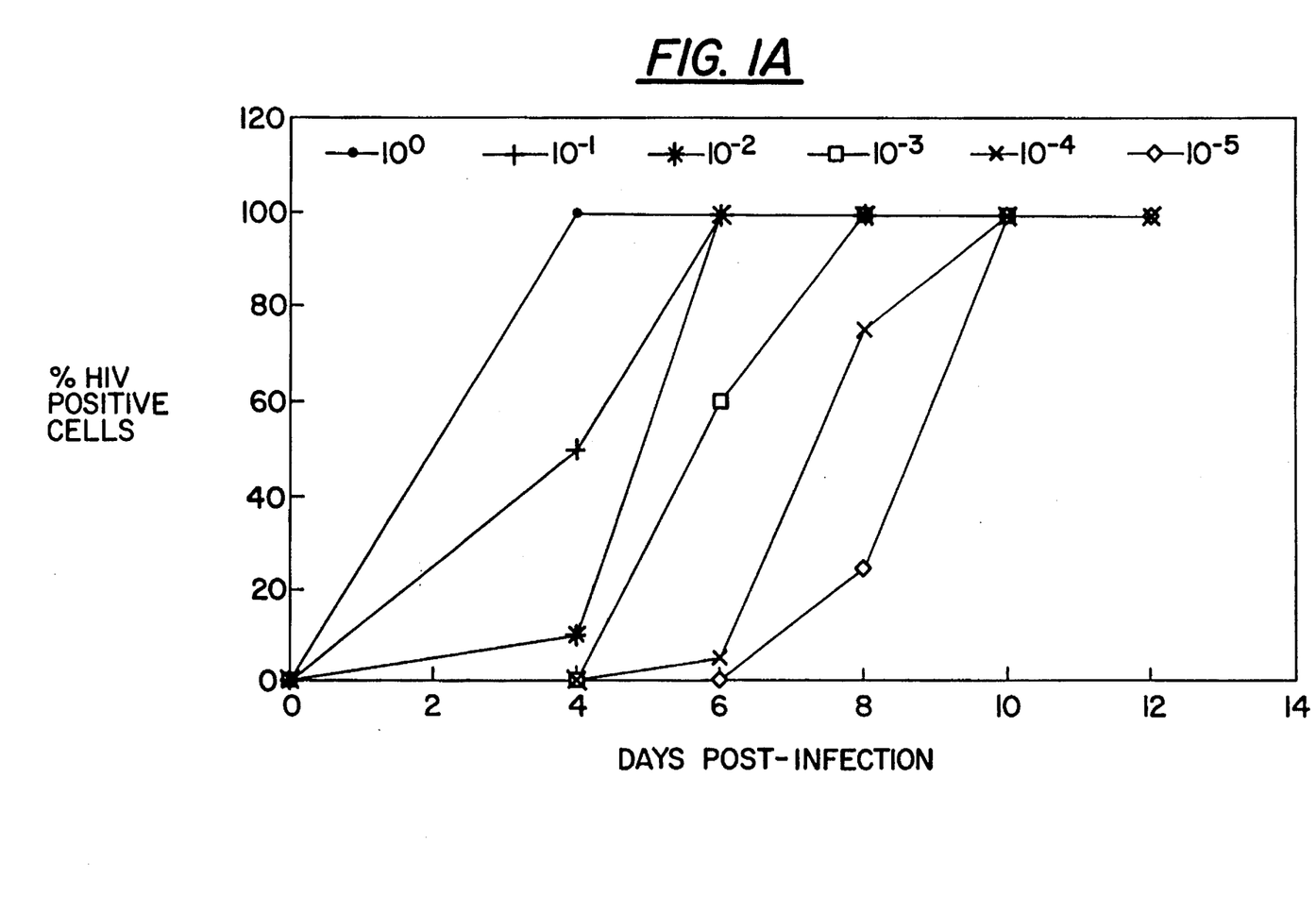
FIG. 1A is a graph showing growth of HIV positive cells with respect to time when not treated with sterilant (control).
Figure 1B:
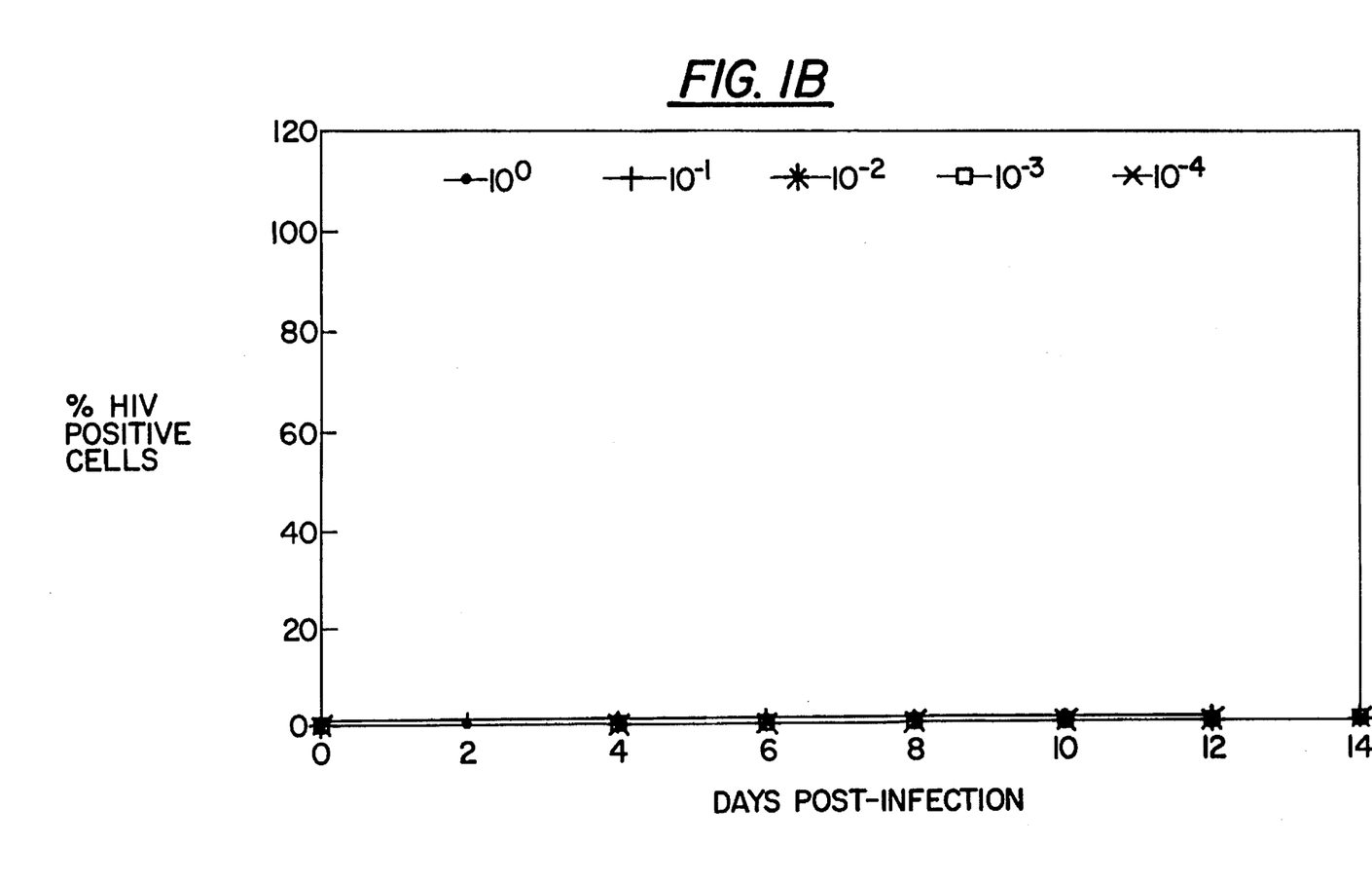
FIG. 1B is a graph showing growth of HIV positive cells with respect to time when treated with 2.5% sterilant of the invention.
Figure 1C:
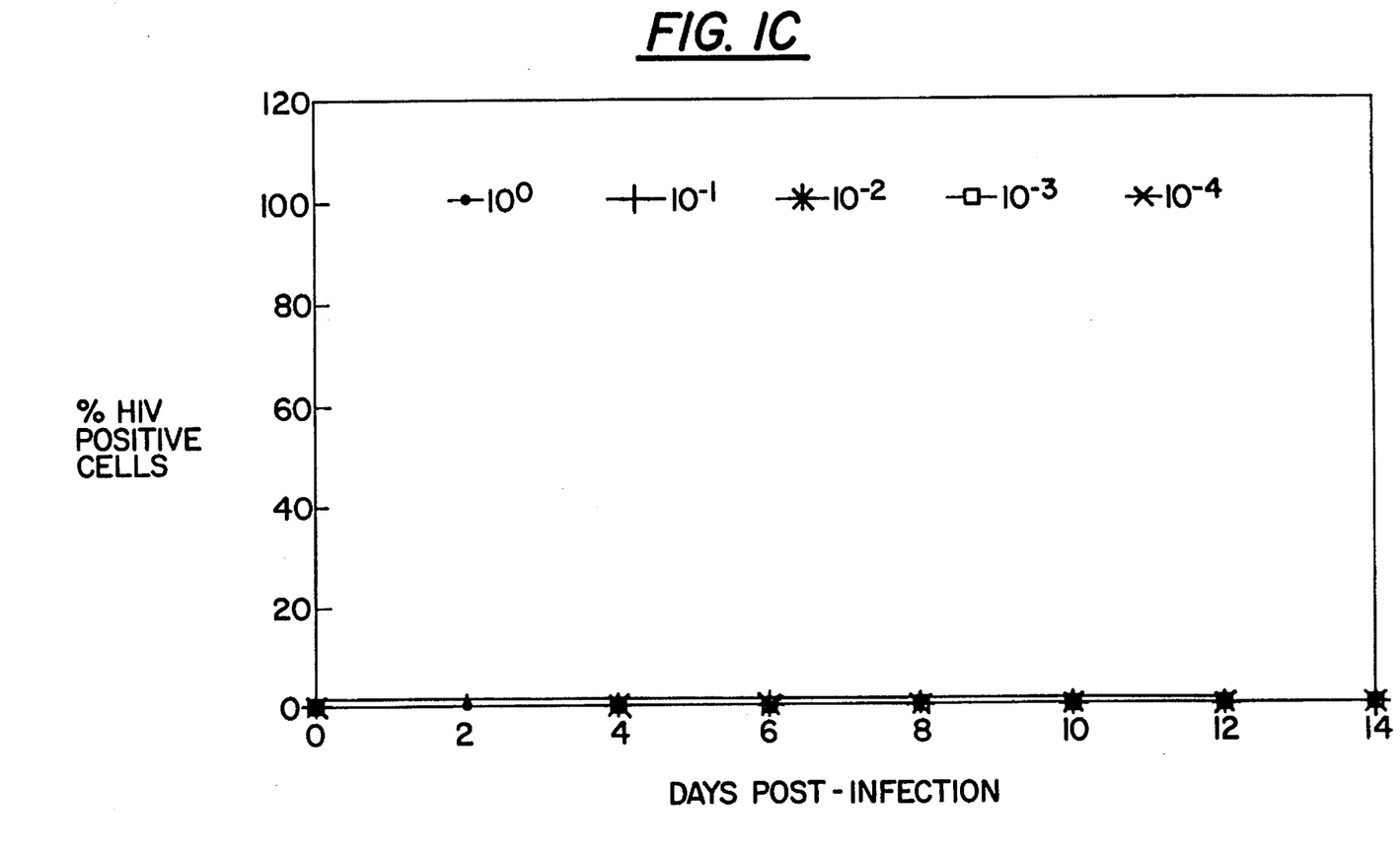
FIG. 1C is a graph showing growth of HIV positive cells with respect to time when treated with 5.0% sterilant of the invention.
Figure 1D:
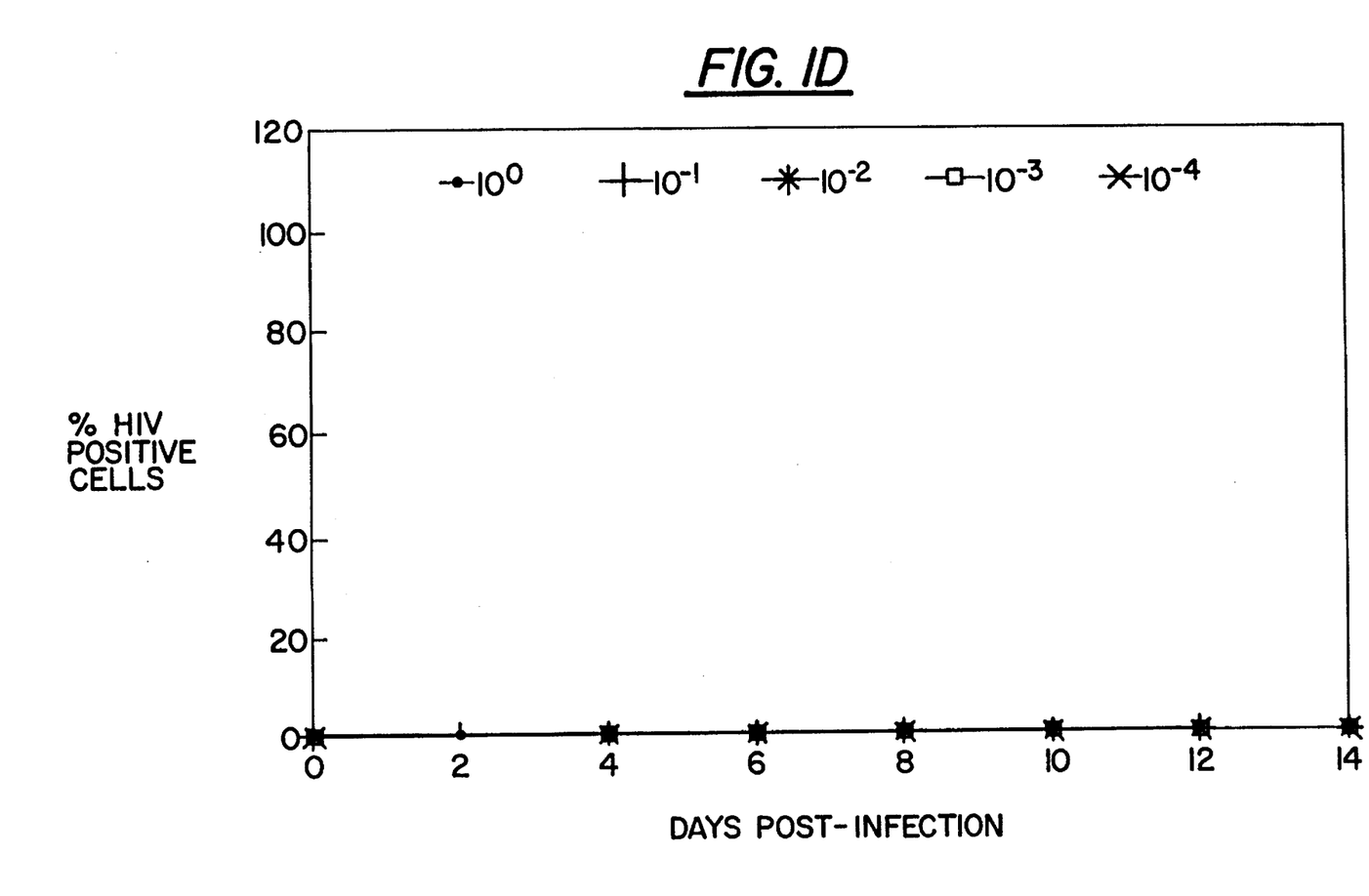
FIG. 1D is a graph showing growth of HIV positive cells with respect to time when treated with 10.0% sterilant of the invention.

With reference to the Figures, FIGS. 1A through 1D represent graphs showing growth of HIV positive cells with respect to time when treated with various concentrations of the sterilant. FIG. 1A is a control to which no sterilant was added. The procedure was carried out as follows:

The sterilant was weighed out and placed in sterile tubes, and 2.5%, 5% and 10% weight per volume solutions were prepared in cell culture media and cooled on ice. Cell culture medium alone, without sterilant, was also placed in a tube as a control (FIG. 1A). An equal volume of HIV positive cells were added to each solution and the control, allowed to incubate on ice for 10 minutes and then each was filtered. Ten-fold dilutions of each virus solution mixture were made in cell culture media for titration of the residual infectious virus.

Twenty-five microliters of the undiluted mixture and each dilution was added to 25 µl of C8166 cells (at $1\times10^4$ per well) in 96-well plates. The plates were then cultured overnight, and the following day 50 µl of media was added to each well. On the fourth day following infection, and every two days thereafter for two weeks, an aliquot of the cells was removed from each well, spotted onto toxoplasmosis slides, fixed with cold acetone and stained for HIV p24 antigen by indirect immunofluorescence. The percentage of p24 HIV-positive cells was determined for each well on each of the test days.

The results are shown graphically in FIGS. 1A–1D, in which FIG. 1A is the control. Treatment of the virus alone in medium without the sterilant did not result in inactivation of the virus. FIG. 1A shows $10^5$ tissue culture infectious doses of virus was present. Treatment of the same virus for 10 minutes with the sterilant powder at the various concentrations completely inactivated the virus, and no infectious virus was detected, even with the undiluted samples (10°). Thus, the powder was able to inactivate at least five $\log_{10}$ of virus under the condition used.

Figure 2A:
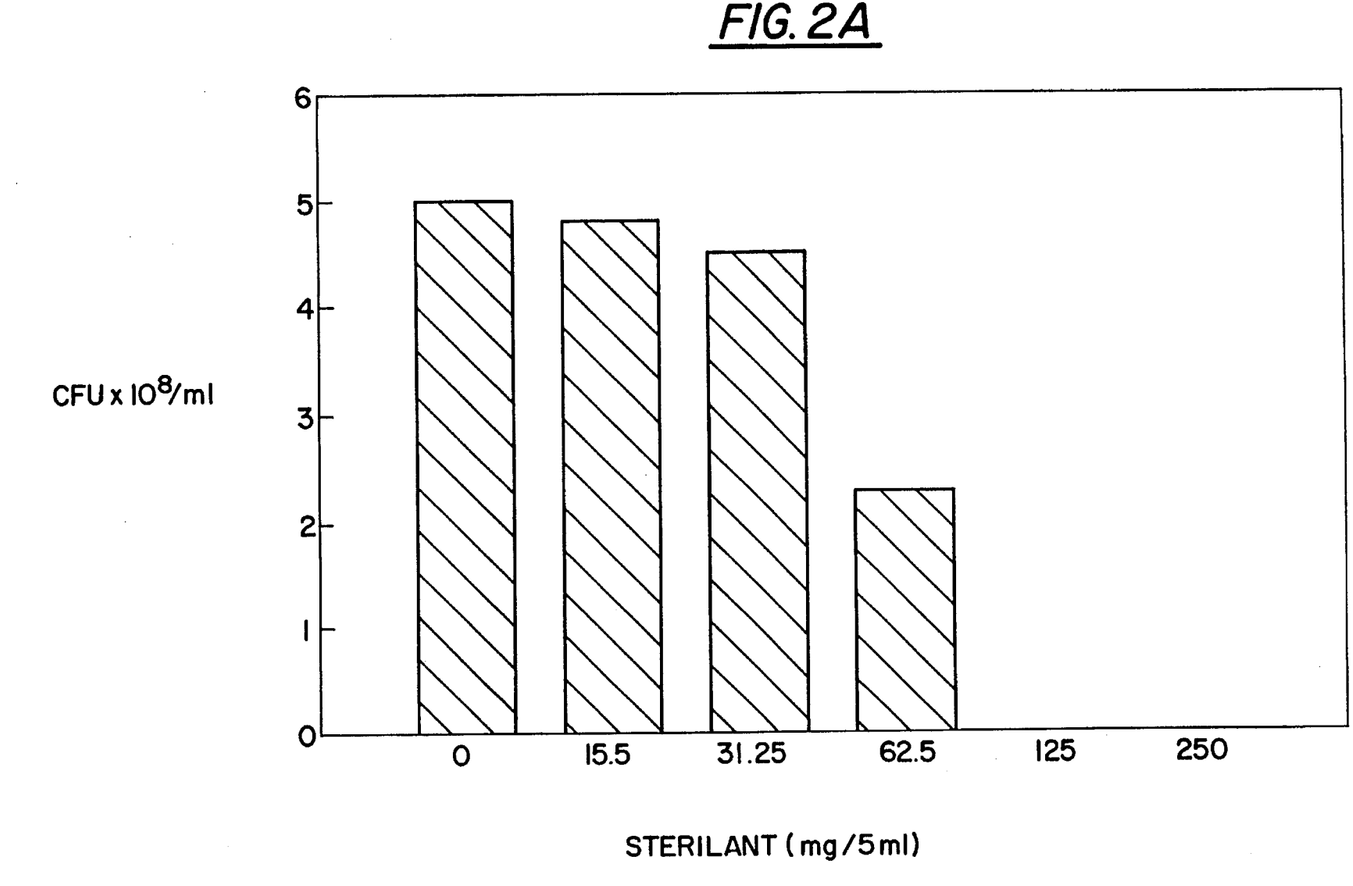
FIG. 2A is a bar graph showing in vitro sensitivity of candida albicans to various concentrations of sterilant.
Figure 2B:
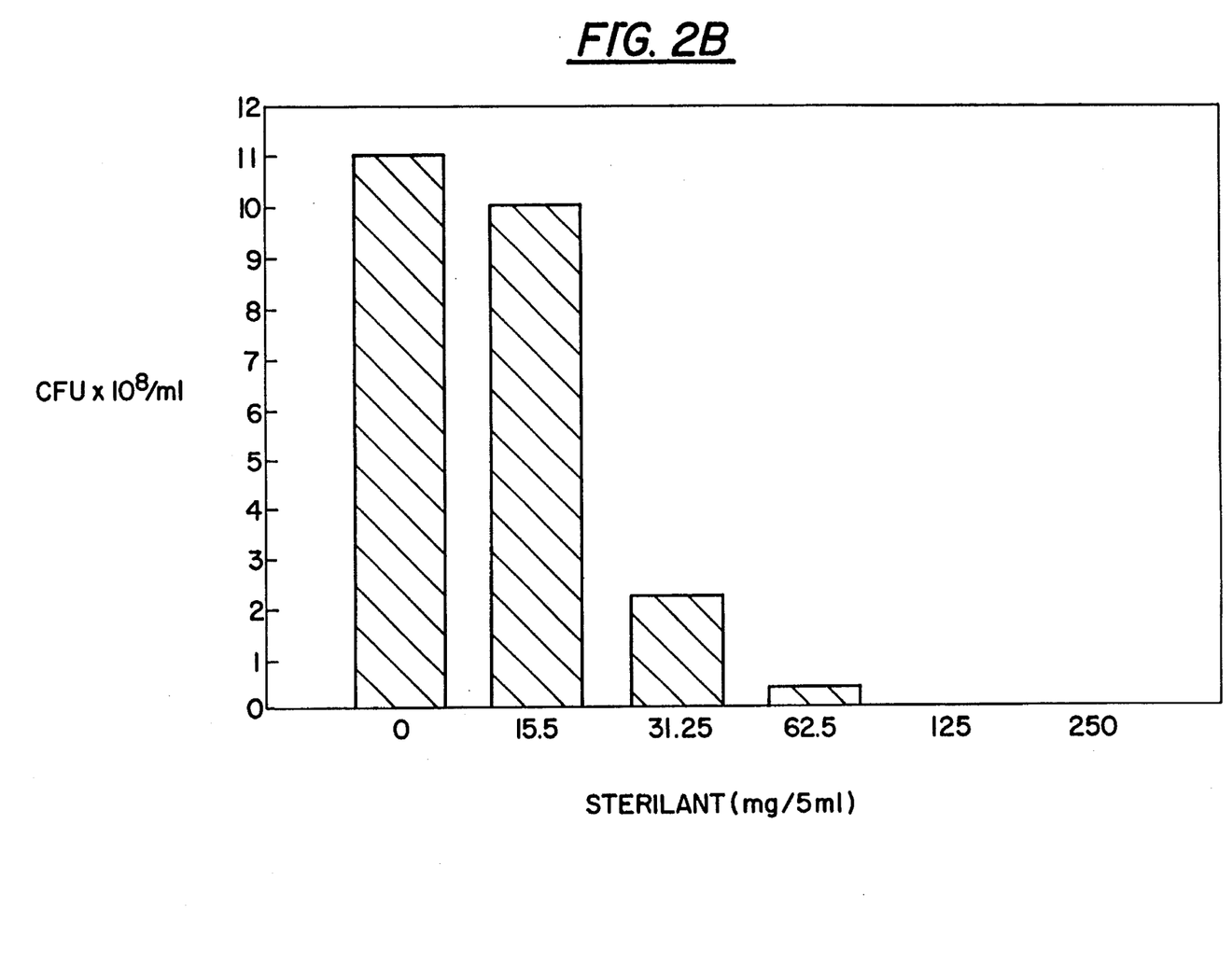
FIG. 2B is a bar graph showing in vitro sensitivity of bacillus subtilus to various concentrations of sterilant.
Figure 2C:
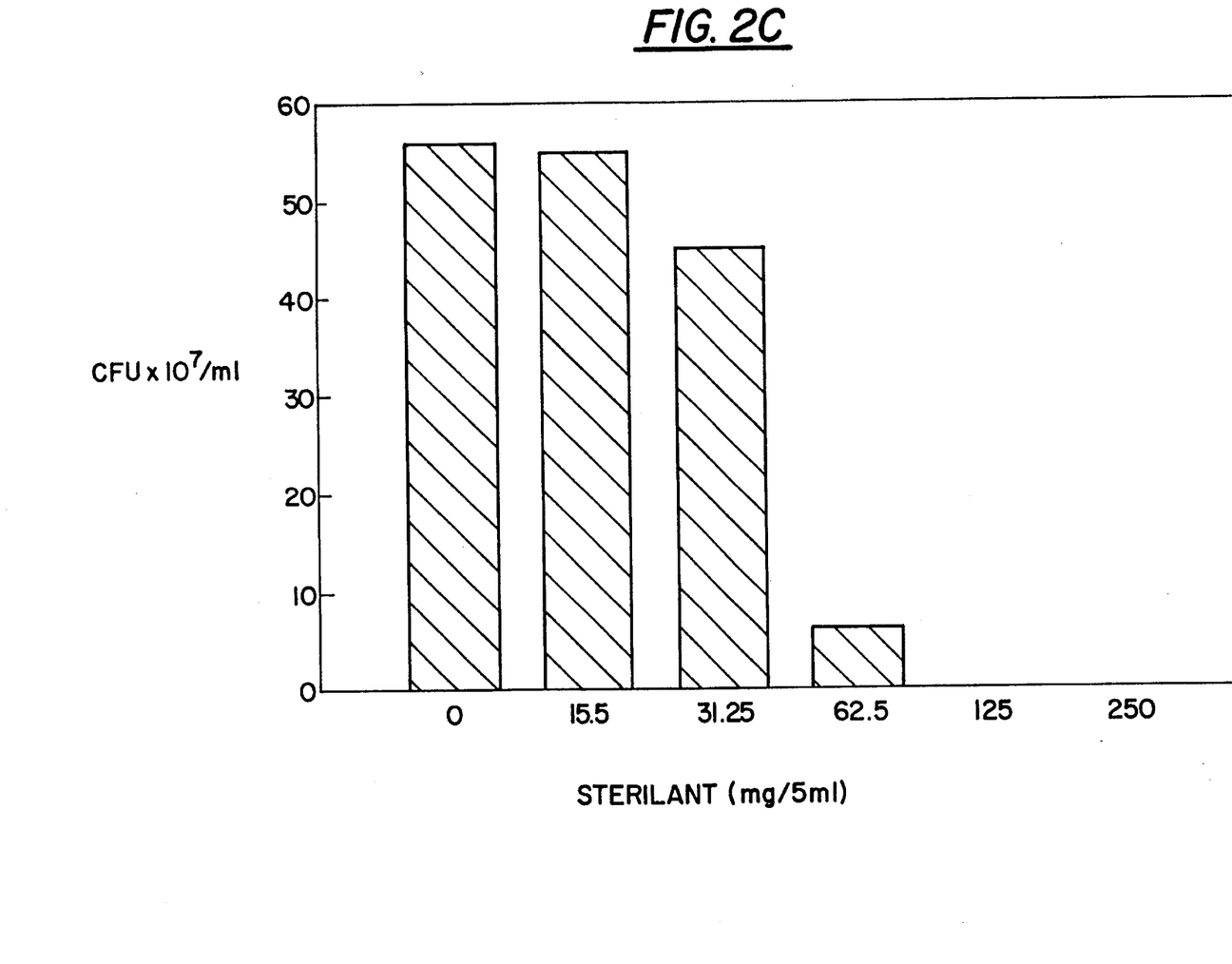
FIG. 2C is a bar graph showing in vitro sensitivity of pseudomonas aeruginosa to various concentrations of sterilant.

Test results on candida albicans, bacillus subtilis and pseudomonas aeruginosa, compared with control samples, are shown in FIGS. 2A, 2B and 2C, respectively and in Table 1 for candida albicans and Table 2 for pseudomonas aeruginosa. Table 1 shows "Recovery of candida albicans with and without sterilant (PMT 100) after processing through the apparatus described in our copending patent application identified above. Table 2 shows "Recovery of pseudomonas aeruginosa with and without sterilant (PMT 100) after processing through the apparatus described in our copending patent application identified above. Incubation was carried out for 30 minutes with various concentrations of sterilant (PMT 100). There is no reduction in cells without the sterilant (PMT 100). Reduction in cells with 5% PMT 100 sterilant is greater than a log reduction of $10_6$.

In the apparatus of our copending patent application, identified above, medical waste material with about 5% sterilant and 15–20% water is processed in the apparatus at a pH of about 10–12.5 for 1–5 minutes at ambient temperature to produce a non-infectious shredded product which is sufficiently dry for disposal without further processing or water removal. The process operates with a minimum of free water as

| Experiment | Load Characteristics | Sample[a] | Theoretical Yield[b] (CFU/10 g) | Actual Yield[c] (CFU/10 g) | Log Reduction |
|---|---|---|---|---|---|
| Without PMT-100 | Low Moisture | 1 | $1.88 \times 10^8$ | $6.8 \times 10^7$ | <10 |
|  |  | 2 | $1.88 \times 10^8$ | $4.1 \times 10^8$ | 0 |
|  |  | 3 | $1.88 \times 10^8$ | $1.8 \times 10^8$ | 0 |
|  |  | 4 | $1.88 \times 10^8$ | $2.1 \times 10^8$ | 0 |
|  |  | 5 | $1.88 \times 10^8$ | $2.2 \times 10^8$ | 0 |
|  | 50% organic | 1 | $1.80 \times 10^8$ | $2.3 \times 10^8$ | 0 |
|  |  | 2 | $1.80 \times 10^8$ | $3.7 \times 10^8$ | 0 |
|  |  | 3 | $1.80 \times 10^8$ | $2.7 \times 10^8$ | 0 |
|  |  | 4 | $1.80 \times 10^8$ | $3.9 \times 10^8$ | 0 |
|  |  | 5 | $1.80 \times 10^8$ | $4.7 \times 10^8$ | 0 |
|  | >70% organic | 1 | $1.73 \times 10^8$ | $2.4 \times 10^8$ | 0 |
|  |  | 2 | $1.73 \times 10^8$ | $7.2 \times 10^8$ | 0 |
|  |  | 3 | $1.73 \times 10^8$ | $2.8 \times 10^8$ | 0 |
|  |  | 4 | $1.73 \times 10^8$ | $3.0 \times 10^8$ | 0 |
|  |  | 5 | $1.73 \times 10^8$ | $5.9 \times 10^8$ | 0 |
| With 5% PMT-100 | Low Moisture | 1 | $1.2 \times 10^8$ | $1.2 \times 10^3$* | $10^5$ |
|  |  | 2 | $1.2 \times 10^8$ | $<10^2$ | $>10^6$ |
|  |  | 3 | $1.2 \times 10^8$ | $<10^2$ | $>10^6$ |
|  |  | 4 | $1.2 \times 10^8$ | $<10^2$ | $>10^6$ |
|  |  | 5 | $1.2 \times 10^8$ | $<10^2$ | $>10^6$ |
|  | 50% organic | 1 | $1.1 \times 10^8$ | $1.1 \times 10^2$* | $10^6$ |
|  |  | 2 | $1.1 \times 10^8$ | $<10^2$ | $>10^6$ |
|  |  | 3 | $1.1 \times 10^8$ | $2.0 \times 10^2$* | $5.5 \times 10^5$ |
|  |  | 4 | $1.1 \times 10^8$ | $<10^2$ | $>10^6$ |
|  |  | 5 | $1.1 \times 10^8$ | $<10^2$ | $>10^6$ |
|  | >70% organic | 1 | $8.6 \times 10^7$ | $<10^2$ | $>10^6$ |
|  |  | 2 | $8.6 \times 10^7$ | $<10^2$ | $>10^6$ |
|  |  | 3 | $8.6 \times 10^7$ | $<10^2$ | $>10^6$ |
|  |  | 4 | $8.6 \times 10^7$ | $<10^2$ | $>10^6$ |
|  |  | 5 | $8.6 \times 10^7$ | $<10^2$ | $>10^6$ |
| Without PMT-100 | Low Moisture | 1 | $1.3 \times 10^7$ | $2.1 \times 10^7$ | 0 |
|  |  | 2 | $1.3 \times 10^7$ | $2.4 \times 10^7$ | 0 |
|  |  | 3 | $1.3 \times 10^7$ | $1.8 \times 10^7$ | 0 |
|  |  | 4 | $1.3 \times 10^7$ | $2.1 \times 10^7$ | 0 |
|  |  | 5 | $1.3 \times 10^7$ | $1.9 \times 10^7$ | 0 |
|  | 50% organic | 1 | $9.3 \times 10^6$ | $1.1 \times 10^7$ | 0 |
|  |  | 2 | $9.3 \times 10^6$ | $1.2 \times 10^7$ | 0 |
|  |  | 3 | $9.3 \times 10^6$ | $9.4 \times 10^6$ | 0 |
|  |  | 4 | $9.3 \times 10^6$ | $1.3 \times 10^7$ | 0 |
|  |  | 5 | $9.3 \times 10^6$ | $1.2 \times 10^7$ | 0 |
|  | >70% organic | 1 | $1.4 \times 10^7$ | $2.2 \times 10^7$ | 0 |
|  |  | 2 | $1.4 \times 10^7$ | $2.1 \times 10^7$ | 0 |
|  |  | 3 | $1.4 \times 10^7$ | $1.8 \times 10^7$ | 0 |
|  |  | 4 | $1.4 \times 10^7$ | $1.7 \times 10^7$ | 0 |
|  |  | 5 | $1.4 \times 10^7$ | $1.9 \times 10^7$ | 0 |
| With 5% PMT-100 | Low Moisture | 1 | $1.3 \times 10^7$ | $<10^1$ | $>10^6$ |
|  |  | 2 | $1.3 \times 10^7$ | $<10^1$ | $>10^6$ |
|  |  | 3 | $1.3 \times 10^7$ | $1.1 \times 10^2$* | $1.1 \times 10^5$ |
|  |  | 4 | $1.3 \times 10^7$ | $<10^1$ | $>10^6$ |
|  |  | 5 | $1.3 \times 10^7$ | $<10^1$ | $>10^6$ |
|  | 50% organic | 1 | $1.2 \times 10^7$ | $<10^1$ | $>10^6$ |
|  |  | 2 | $1.2 \times 10^7$ | $<10^1$ | $>10^6$ |
|  |  | 3 | $1.2 \times 10^7$ | $<10^1$ | $>10^6$ |
|  |  | 4 | $1.2 \times 10^7$ | $<10^1$ | $>10^6$ |
|  |  | 5 | $1.2 \times 10^7$ | $<10^1$ | $>10^6$ |
|  | >70% organic | 1 | $9.4 \times 10^6$ | $<10^1$ | $>10^6$ |
|  |  | 2 | $9.4 \times 10^6$ | $<10^1$ | $>10^6$ |
|  |  | 3 | $9.4 \times 10^6$ | $<10^1$ | $>10^6$ |
|  |  | 4 | $9.4 \times 10^6$ | $<10^1$ | $>10^6$ |
|  |  | 5 | $9.4 \times 10^6$ | $<10^1$ | $>10^6$ |

[a]Five samples (50–75 g) were collected during processing; The first was taken on the first exited material, other samples were taken at ~45 sec. intervals. Total run times were ~5 min. Challenge loads of medical waste ranged from 5410 g–8989 g. Specific composition of each load is available. Samples were transported to the laboratory and processing initiated after 24 hr. at room temperature. 10 g samples were utilized an diluted with 40 ml of 0.1N $KH_2 PO_4$ and 50 ml PBS. This neutralized samples to pH 7.0 Samples were agitated by hand for 30 sec. Additional dilutions were made in 4.5 ml of PBS. Samples (0.1 ml) were spread in triplicate on L. agar, MacConkey lactose agar or Sabouraud's dextrose agar. Plates were incubated at 37° C. for 16 h. and counted.
[b]Theoretical yield represents the challenge dose of the microorganisms as dispersed in the defined medical waste sample expressed as CFU/10 g.
[c]Actual yield is the recovery of microorganisms based on the recovery of CFU on agar plates using triplicate samples < - indicates no recovery based on lowest dilution plated.
*Significant contaminants may have skewed count the sterilant is hygroscopic and free water is readily absorbed to produce a shredded non-infectious product.

While the invention has been described above with respect to certain embodiments thereof, it will be appreciated by one skilled in the art that variations and modifications may be made without departing from the spirit and scope of the invention.

What is claimed is:

1. A sterilant composition for treating shredded hospital medical waste material during size reduction in a shredding apparatus and for rendering pathogens in shredded medical waste non-infectious, said sterilant composition comprising calcium oxide and calcium carbonate mixed in a ratio of 20:80 to 60:40, by weight which, when mixed with pathogen-containing shredded hospital medical waste material and water in a shredding apparatus during size reduction of said hospital waste material, reacts to render the pathogens therein non-infectious at a pH of about 10–12.5 and a temperature of about 5°–35° C., to produce a non-infectious product.

2. A sterilant according to claim 1 wherein the calcium oxide and calcium carbonate are mixed in a ratio of 40:60 to 60:40.

3. A sterilant according to claim 1 wherein the sterilant renders the pathogens non-infectious at a pH of about 11.0–12.0.

4. A sterilant according to claim 1 wherein the sterilant renders the pathogens non-infectious at a temperature of about 20°–30° C.

5. A sterilant according to claim 1 wherein the sterilant renders the pathogens non-infectious by denaturing nucleic acids and proteins therein.

6. A sterilant according to claim 1 further comprising at least one member selected from the group consisting of magnesium oxide, aluminum oxide, silicon dioxide, ferric oxide, calcium sulfate, potassium oxide and titanium dioxide.

7. A method of sterilizing pathogen-containing hospital medical waste material during size reduction in a shredding apparatus, comprising mixing shredded hospital medical waste material with a sterilant composition for rendering pathogens in the waste material non-infectious, said sterilant composition comprising calcium oxide and calcium carbonate mixed in a ratio of 20:80 to 60:40, by weight, reacting said sterilant composition with said pathogen-containing material and water at a pH of about 10–12.5 and a temperature of 5°–35° C., rendering said pathogens non-infectious and producing a non-infectious product.

8. A method according to claim 7 wherein the calcium oxide and calcium carbonate are mixed in a ratio of 40:60 to 60:40.

9. A method according to claim 7 wherein the sterilant renders the pathogens non-infectious at a pH of about 11.0–12.0.

10. A method according to claim 7 wherein the sterilant renders the pathogens non-infectious at a temperature of about 20°–30° C.

11. A method according to claim 7 comprising rendering the pathogens non-infectious by denaturing nucleic acids and proteins therein.

12. A method according to claim 7 wherein the method comprises adding at least one member selected from the group consisting of magnesium oxide, aluminum oxide, silicon dioxide, ferric oxide, calcium sulfate, potassium oxide and titanium dioxide to the sterilant mixture.

13. A method according to claim 7 wherein the pathogen containing medical waste material is rendered sterile by passage through a shredding apparatus in combination with the sterilant composition during a time period of 1 to 5 minutes.

* * * * *